United States Patent
Carpenter

(10) Patent No.: US 11,950,913 B2
(45) Date of Patent: Apr. 9, 2024

(54) ELECTROCARDIOGRAM SENSOR

(71) Applicant: SUREPULSE MEDICAL LIMITED, Derby (GB)

(72) Inventor: James Carpenter, Derby (GB)

(73) Assignee: SUREPULSE MEDICAL LIMITED, Derby (GB)

(*) Notice: Subject to any disclaimer, the term of this patent is extended or adjusted under 35 U.S.C. 154(b) by 871 days.

(21) Appl. No.: 16/606,261

(22) PCT Filed: Apr. 23, 2018

(86) PCT No.: PCT/GB2018/051049
§ 371 (c)(1),
(2) Date: Oct. 18, 2019

(87) PCT Pub. No.: WO2018/193271
PCT Pub. Date: Oct. 25, 2018

(65) Prior Publication Data
US 2020/0037912 A1  Feb. 6, 2020

(30) Foreign Application Priority Data

Apr. 21, 2017 (GB) .................................. 1706354

(51) Int. Cl.
*A61B 5/28* (2021.01)
*A61B 5/282* (2021.01)
*A61B 5/322* (2021.01)

(52) U.S. Cl.
CPC .............. *A61B 5/282* (2021.01); *A61B 5/28* (2021.01); *A61B 5/322* (2021.01);
(Continued)

(58) Field of Classification Search
CPC ........ A61B 2503/045; A61B 2562/164; A61B 2562/227; A61B 5/252; A61B 5/282; A61B 5/322
See application file for complete search history.

(56) References Cited

U.S. PATENT DOCUMENTS 4,583,549 A * 4/1986 Manoli ................ A61B 5/411
600/397
5,865,741 A * 2/1999 Kelly .................... A61B 5/282
600/386
(Continued)

FOREIGN PATENT DOCUMENTS

CN  1946826 A   4/2007
EP  1249204 A1  10/2002
(Continued)

OTHER PUBLICATIONS

First Office Action issued in corresponding CN application No. 2018800260062 dated Jan. 4, 2022.
(Continued)

*Primary Examiner* — Amanda K Hulbert
(74) *Attorney, Agent, or Firm* — Vorys, Sater, Seymour and Pease, LLP

(57) ABSTRACT

An electrocardiogram sensor (400) is provided, comprising an electrode array (100), comprising a substrate (102) interconnecting three or more spaced apart electrodes (101*a-c*); and a flexible sheet (200) having a greater areal extent than that of the electrode array (100). The flexible sheet (200) is configured to secure the electrodes (101*a-c*) to the body of a subject.

19 Claims, 6 Drawing Sheets

(52) U.S. Cl.
CPC ... *A61B 2503/045* (2013.01); *A61B 2562/164* (2013.01); *A61B 2562/227* (2013.01)

(56) References Cited

U.S. PATENT DOCUMENTS

| | | | |
|---|---|---|---|
| 6,453,186 B1* | 9/2002 | Lovejoy | A61B 5/282 600/386 |
| 2004/0176674 A1* | 9/2004 | Nazeri | A61B 5/061 600/382 |
| 2007/0162099 A1 | 7/2007 | Hyatt et al. | |
| 2009/0076364 A1 | 3/2009 | Libbus et al. | |
| 2013/0325096 A1 | 12/2013 | Dupelle et al. | |
| 2015/0005589 A1* | 1/2015 | Bly | A61B 5/6801 600/301 |
| 2015/0282734 A1* | 10/2015 | Schweikert | A61B 5/318 600/424 |
| 2017/0273591 A1* | 9/2017 | Agus | A61B 5/6823 |

FOREIGN PATENT DOCUMENTS

| | | |
|---|---|---|
| EP | 1739149 A1 | 3/2007 |
| GB | 2527031 A | 12/2015 |
| WO | 2008068695 A1 | 6/2008 |
| WO | 2018193271 A1 | 10/2018 |

OTHER PUBLICATIONS

Search Report issued in corresponding CN application No. 2018800260062 dated Jan. 4, 2022.

ISRWO dated Jun. 25, 2018 in related PCT/GB2018/051049 application filed on Apr. 23, 2018.

Chinese Office Action from corresponding CN Application No. 201880026006.2 dated Nov. 29, 2022.

EP Examination Report from corresponding EP Application No. 18724982 dated Oct. 31, 2022.

* cited by examiner

ELECTROCARDIOGRAM SENSOR

FIELD OF THE INVENTION

The invention relates to an electrocardiogram sensor having electrodes arranged on a substrate and having a flexible sheet to allow the sensor to be attached to a subject, preferably without the need for adhesive.

BACKGROUND

Obtaining a reliable measure of heart rate after birth in newborn babies is difficult, particularly for those requiring resuscitation or stabilisation. Pulse oximeters typically do not work well in the first ~5 minutes because of poor perfusion to the limbs, where transmission mode pulse oximeter probes are usually placed. Whilst electrocardiograms (ECG) can theoretically work, application of the ECG electrodes is problematic for a few reasons. Firstly, the requirement for a rapid measure of heart rate is generally precluded by the time taken to apply multiple (usually three or four) electrodes to the baby's skin. The emphasis for the clinical team must be primarily on the baby, not on applying ECG electrodes. Secondly, since the baby will be covered in blood and vernix from the birth, adhesion can be problematic. Although the babies can be wiped down, vernix can still remain. This makes application of undivided ECG probes difficult and they can easily fall off. However if greater adhesive strength is used, this can result in skin stripping when the electrodes are removed, particularly in premature babies with weaker or thinner skin. Thirdly, premature babies are typically placed into plastic bags to keep them warm. A long delay, such as that required to reliably apply ECG electrodes, can increase the risk of hypothermia.

SUMMARY OF THE INVENTION

In accordance with a first aspect of the invention there is provided an electrocardiogram sensor comprising:
 an electrode array comprising a substrate interconnecting three or more spaced apart electrodes; and
 a flexible sheet having a greater areal extent than that of the electrode array and configured to secure the electrodes to the body of a subject.

The invention allows for an ECG sensor array that can be applied rapidly to provide a reliable measure of heart rate, particularly for newborn babies. The use of a flexible sheet in addition to the substrate for the electrodes allows for an additional area for contacting the skin of the subject, allowing for surface tension between the sheet and the subject to secure the electrodes to the skin without the need for adhesive.

The flexible sheet may comprise holes at positions corresponding to the electrodes, each hole being smaller than a corresponding electrode. This enables the flexible sheet to be provided as a separate unit to the electrode array, with the holes in the flexible sheet being smaller than the electrodes so that the electrodes can be held in place against the subject by the sheet.

The areal extent of the flexible sheet may be greater than twice that of the electrode array. The areal extent may for example be between 2 and 3 times that of the electrode array, thereby allowing for a greater area of contact with the subject without the flexible sheet becoming unwieldy.

The flexible sheet and the electrodes are preferably non-adhesive, as surface tension (or dispersive adhesion) alone is sufficient to maintain contact with the subject (without the need for a tacky or adhesive material).

The substrate may comprise a sheet of a first polymeric material and the flexible sheet may comprise a sheet of a second polymeric material, the second polymeric material having a lower stiffness than the first polymeric material. Selecting a lower stiffness for the second polymeric material allows the flexible sheet to be easier to conform to the shape of the subject's body, while the first polymeric material maintains a required spacing between the electrodes. Alternatively, the flexible sheet may comprise a sheet of paper or any biocompatible substance that provides sufficient adhesion between the subject and flexible sheet.

The first polymeric material may for example have a tensile stiffness of greater than 2 GPa while the second polymeric material has a tensile stiffness of less than 1 GPa.

The first polymeric material may for example by polyethylene terephthalate or a polyamide. The second polymeric material may be polyethylene or polyvinyl chloride.

The flexible sheet may have a thickness of less than 50 micrometres, less than 25 micrometres or less than 12.5 micrometres. This range of thickness allows the flexible sheet to be sufficiently flexible to conform to the subject's body without resisting being bent. The substrate may have a thickness of less than 150 micrometres, less than 100 micrometres or less than 50 micrometres. The substrate will typically be thicker than the flexible sheet, to ensure sufficient rigidity to maintain separation of the electrodes.

In some examples the flexible sheet and the substrate are integrated, while in others the sheet and substrate may be provided separately and assembled prior to use.

The electrocardiogram sensor may comprise a dock comprising electrical contacts for contacting with a corresponding module, the electrical contacts connected to the electrodes of the sensor. The dock may be provided at a distal end of a connector extending from the substrate, or may be provided at a central region of the substrate between the electrodes. In other examples the electrocardiogram sensor may comprise a cable connected to the electrodes via connections on the substrate.

In accordance with a second aspect of the invention there is provided an electrocardiogram sensor system comprising:
 the electrocardiogram sensor of the first aspect;
 a module connectable to the dock on the substrate; and
 a processing a display unit wirelessly connectable to the module,
 wherein the module is configured to wirelessly transmit data obtained from the electrodes of the electrocardiogram sensor for display on the processing and display unit.

In accordance with a third aspect of the invention there is provided a method of applying an electrocardiogram sensor according to the first aspect to a subject, the method comprising:
 applying an electrically conductive gel to each of the electrodes;
 applying the flexible sheet and the electrodes to the subject,
 wherein the electrodes and the flexible sheet are held in place against the subject by surface tension or dispersive adhesion.

The dispersive adhesion may arise without the need for an adhesive or tacky material, as a result of wetting of sufficient area of the flexible sheet by fluids on the surface of the subject.

The method may comprise arranging the flexible substrate such that each of the electrodes is aligned with a corresponding hole in the flexible sheet, which is applicable to examples where the flexible sheet is provided as a separate part to the electrode array.

The method may comprise applying a gel, optionally an electrically conductive gel, to a side of the flexible sheet prior to applying the flexible sheet to the subject.

The subject is typically a newborn child. The electrodes and flexible sheet may be applied to the back of the newborn child, or in some cases to the front. The flexible sheet may in some cases be wrapped around the torso of the newborn child.

DETAILED DESCRIPTION

The invention is described in further detail below by way of example and with reference to the accompanying drawings, in which.

Figure 1:
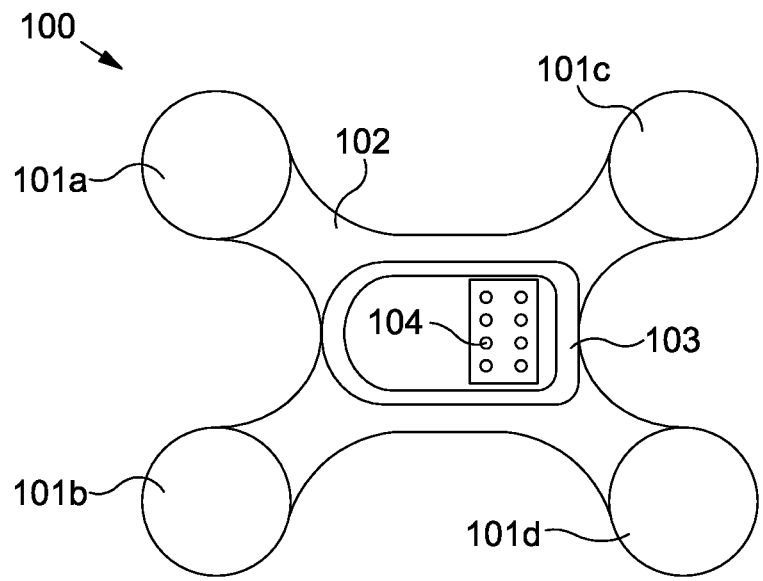
FIG. 1 is a schematic plan view of an example electrode array on a substrate.

An example electrode array 100 for an electrocardiogram sensor is illustrated in FIG. 1. The array 100, which is typically for single use, has at least three electrodes arranged in an array, which may for example be a square, triangular, rectangular or circular arrangement. A rectangular arrangement having four electrodes is shown in FIG. 1. The electrodes 101a-d are mounted on a common substrate 102 that interconnects the spaced apart electrodes 101a-d. The substrate 102 may be made from a material such as polyethylene terephthalate (PET), which has a stiffness that is suitable for maintaining the electrodes 101a-d in a fixed relative position while allowing the substrate 102 to bend to conform to the shape of the subject's body. The substrate 102 contains conductive tracks (not shown) that interface the electrodes 101a-d with a dock 103 containing electrical contacts 104 for connecting the array 100 to a measurement module. As shown in FIG. 1 the dock 103 is provided in a central region of the array 100, although in other arrangements the dock 103 may be provided in other positions.

Figure 8:
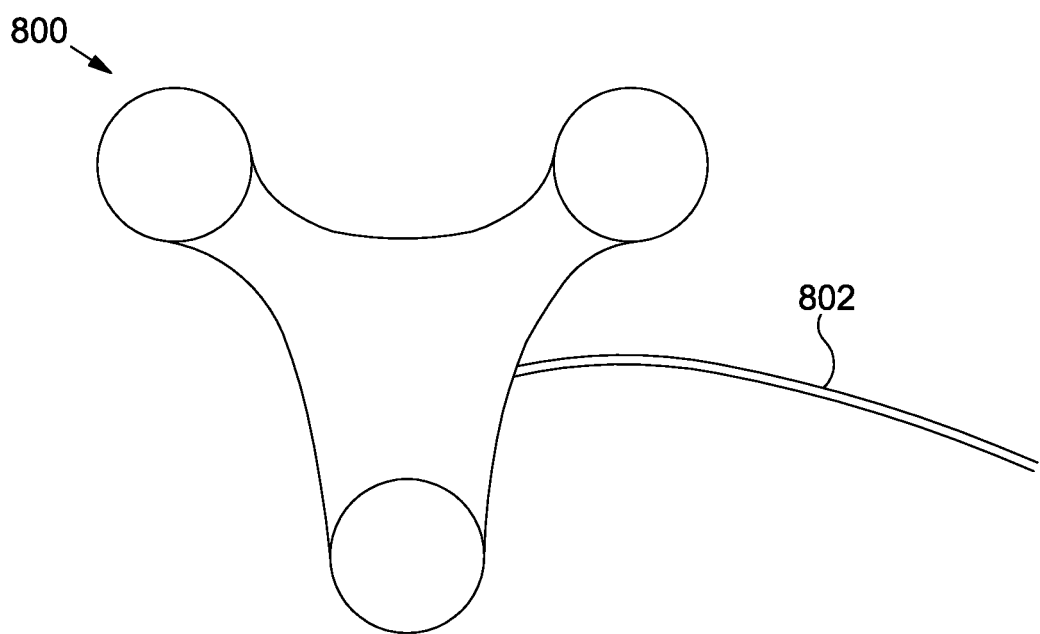
FIG. 8 is a schematic plan view of a further alternative example electrode array with a shielded cable for connection to an ECG monitor.

The dock 103 may be made from a hard plastic, normally PC/ABS (polycarbonate/acrylonitrile butadiene styrene), and preferably contains a ferrous element to hold a connector module (not shown in FIG. 1) in place using a magnetic contact. Sprung contacts on either the module or the dock 103 allow a reliable electrical connection to be made to flat contacts on the opposing dock or the module. The dock 103 could also be provided at the distal end of a flat flexible extension cable, either as part of the substrate 102 or using a different material containing conductive tracks, as shown in the alternative arrangement in FIG. 6, which may be more suitable if the array 100 is placed on the back of a baby, where a flat comfortable profile for the array is required. Alternatively if an existing wired ECG monitor is available then the array could be used with a cable connecting the electrodes to the existing wired ECG monitor, as shown in FIG. 8.

The electrodes 101a-d may be wet gel, hydrogel or dry contact type electrodes. For a low impedance connection a saline wet or hydrogel of low resistivity is preferably used when connecting the array 100 to a subject.

Figure 2:
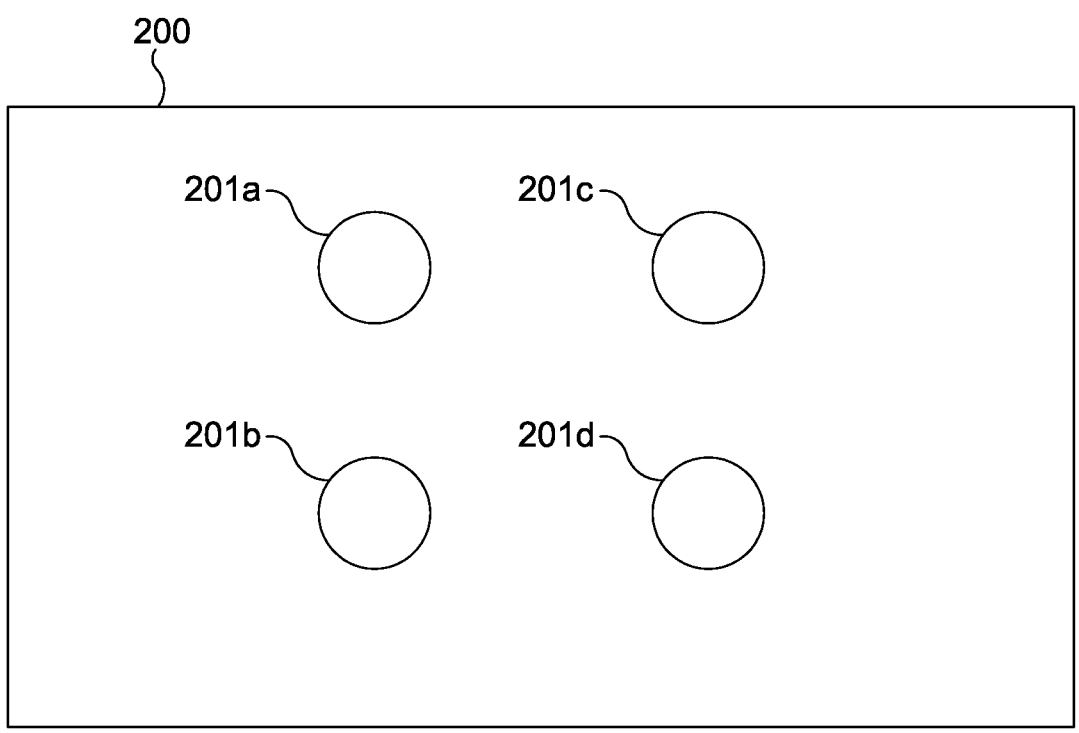
FIG. 2 is a schematic plan view of a flexible sheet with holes for attachment to the electrode array of FIG. 1.

A flexible sheet 200, an example of which is shown in FIG. 2, can be used to secure the connection between the electrodes 101a-d and the skin of the subject by increasing the surface tension between the sensor and the subject. The array 100 could hold itself in place with a conductive gel or solution, which may provide enough surface tension to adhere the array to the subject, but there is a risk that the array 100 will come loose, particularly if the subject is moved. A flexible sheet 200 extending beyond the array 100, i.e. having a greater areal extent than that of the array 100, is beneficial in providing additional surface area for the array to stay in place using surface tension alone. The flexible sheet 200 could be integrated with the array 100 and substrate 102, or be provided as a separate layer to be assembled prior to use. The areal extent of the flexible sheet 200 is preferably at least twice that of the electrode array 100, and may in some cases be up to three times that of the electrode array 100. The flexible sheet is preferably of a generally rectangular form, having a length that is over 1.5 times that of its width, and in some cases may be up to three times that of its width.

A suitable size for the sheet 200 would be such that the length covers at least one side of the torso of the baby and the width is no higher than the abdomen of the baby. Example dimensions of the sheet are between 8 and 15 cm in width and at least 10 cm in length. The length may be more variable than the width, and may for example be up to 20 or 30 cm, with a longer sheet being able to be wrapped around the torso of the baby for additional security of contact. The sheet 200 shown in FIG. 2 has a number of holes 201a-d equal to the number of electrodes in the array 100. In cases where the sheet 200 is provided as a separate component, the holes 201a-d are slightly smaller than that of the corresponding electrodes 101a-d, which allows the electrodes 101a-d to protrude through the holes 201a-d and remain in place when the sheet 200 is affixed to the subject. Alternatively, the electrode array 101, flexible sheet 200 and flexible substrate may form one integrated unit.

In some embodiments, the electrodes 101a-d may sit proud of the sheet. This improves the connection between the electrodes 101a-d and the skin of the subject.

The electrodes 101a-d face towards the skin of the subject. However, the electrical connections to the dock 103 typically point upwards (i.e. away from the subject). In order to secure an electrical connection between the electrodes 101a-d and the dock 103, through holes (not shown) between the flexible sheet 200 and the substrate 102 may be provided, allowing the conductive tracks (not shown) to pass from the underside of the sheet 200 and substrate 102 to the top side. Alternatively, the conductive tracks may pass from the electrodes to the edge of the flexible sheet 200, and fold over to the top side. This issue is particularly pertinent where the electrode array 101, flexible sheet 200 and flexible substrate form one integrated unit.

A conductive ECG gel smeared over each of the electrodes 101*a-d* provides the required electrical coupling between the electrodes 101*a-d* and the skin of the subject and provides an amount of adhesion due to surface tension. Further amounts of gel may be used on the sheet 200, provided this does not short circuit any of the electrodes, to provide additional surface tension between the sheet 200 and the skin of the subject. The sheet alone, however, may provide sufficient adhesion, particularly if the subject is still wet and/or if the sheet is sufficiently thin and elastic.

The conductive ECG gel may be a wet gel. The wet gel may have a thickness of approximately 2-3 mm and be held in an open cell sponge carrier. Further, a moat or wall arrangement may surround the edge of each electrode 101*a-d*. The moat extends below the base of the electrode, and may form an approximate "U"-shape 1-3 mm deep (or 1-3 mm high in the case of a wall) around the edge of each electrode 101*a-d*. The moat or wall may be composed of a more rigid material than that of the flexible sheet 200.

This prevents the wet gel moving from each electrode 101*a-d* over the flexible sheet 200 and substrate 102. A micropore cover may also be provided, which can be placed on the surface of a 'wet gel' electrode. This may reduce the irritation caused by the sponge carrier on the skin of the subject, and help to hold the wet gel in place.

Alternatively, hydrogel may be used. This may remove the need for a sponge carrier, moat and micropore cover.

The sheet 200 may be composed of a soft polymeric material, for example polyethylene or polyvinyl chloride, or in some cases may be composed of paper or any biocompatible substance that provides sufficient surface tension.

For a wet gel, a 1% to 12% saline solution may be suitable (i.e. 1 g NaCl or KCl per litre of water to 12 g NaCl or KCl per litre of water). A conductive gel may have a polyacrylate base, for example an ECG conductive gel available from Dermedics (RTM) International (www.dermedics.com). Other ingredients include sodium chloride and water.

Figure 3:
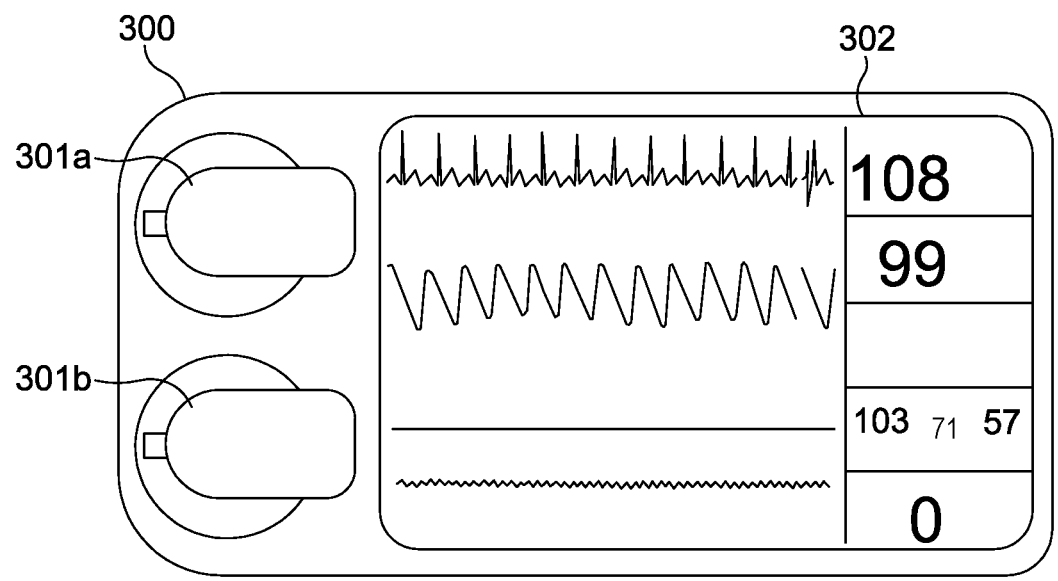
FIG. 3 shows an example display unit with docked modules for connection to an electrode array.

A small electronic module may be provided that provides power and wireless transmission of data obtained from the sensor to a processing and display unit. An example processing and display unit 300 is illustrated in FIG. 3. Two modules 301*a*, 301*b* are shown docked to the processing and display unit 300. Docking the modules 301*a*, 301*b* to the unit 300 allows the modules 301*a*, 301*b* to be recharged and stored when not in use. A display 302 provides ECG and heart rate traces derived from the electrode array 100. The unit 300 is preferably battery powered to allow it to be highly portable.

In order to ensure that the ECG signal can be detected, a difference amplifier with adequate electrode impedance mismatch immunity should be used in the module.

The individual electrode impedance may be measured, to provide notification of any potential operational issues to the user. One method of measuring the impedance may be supplying a low current sinusoidal source to the electrodes, and measuring the voltage generated through each pair of the electrodes, changing one electrode per measurement (i.e. measuring pair AC, BC, BD). Alternatively, impedance can be measured by applying a square wave current and measuring resistance and capacitance of the electrodes sequentially.

Figure 4:
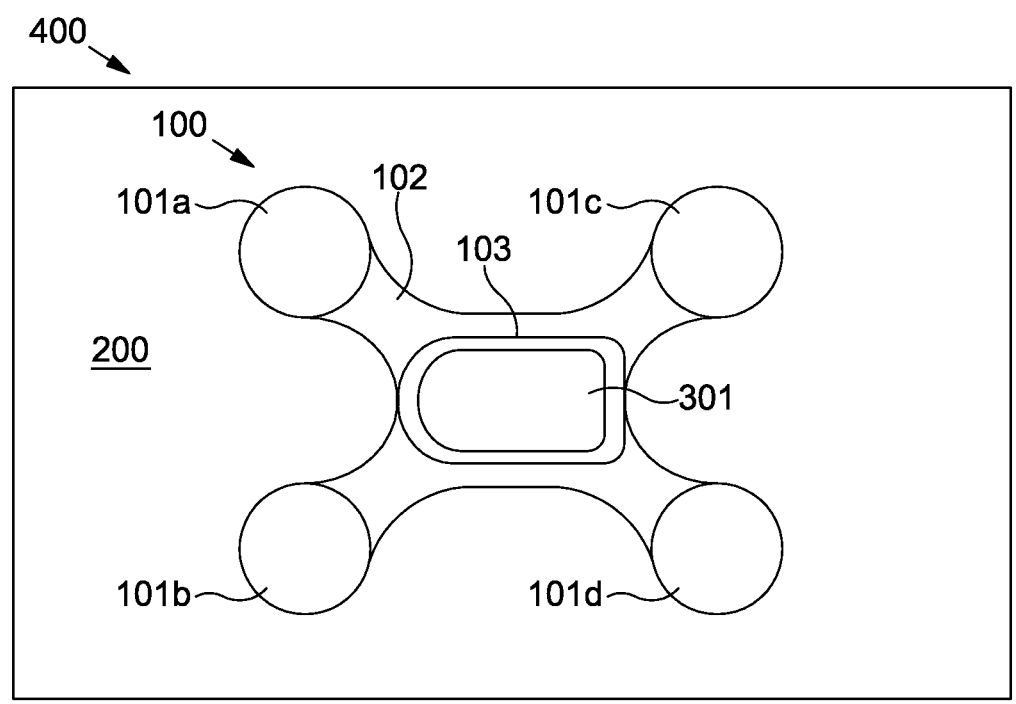
FIG. 4 is a schematic plan view of an example electrode array on a substrate, with a flexible sheet and connection module attached.

For use, one of the modules 301 is taken out of the processing and display unit 300 and attached to the dock 103 in the array 100 when required for vital sign monitoring, as illustrated in the electrocardiogram sensor 400 in FIG. 4.

The raw data from the electrodes 101*a-d* is detected by the module 301. The data can be processed in real time on the module 301 to obtain heart rate (and optionally breathing rate) or the raw data can instead be transmitted by the module 301 to the processing and display unit 300 to process to a heart rate (and optionally breathing rate). Transmitting the data as heart rate rather than raw data reduces the power and bandwidth requirements of the module. As discussed earlier, in alternative examples an existing ECG monitor may be used with a wired connection made from the ECG array directly to the ECG monitor.

An accelerometer/gyroscope and magnetometer in the module 301 may provide useful contextual information such as activity, breathing, orientation etc. This can also facilitate noise removal by adaptive filtering.

When a newborn is being intubated, the forced breathing rate is superimposed on both ECG and PPG baselines. This means that, in addition to measuring the heart rate and breathing rate of the subject, the ECG array may be used for confirming the intubation rate.

The module 301 can additionally provide optical detection capabilities to pick up a photoplethysmogram in multiple wavelengths (e.g. red, infrared and green) which would facilitate the display of oxygen saturation status. The electrode array 100 may comprise additional embedded transmission mode optical sensors for this purpose.

The sheet 200 may be either separately packaged with the array 100 or be integrated with the substrate 102. If the sheet were not used, the substrate with gel alone would need to have adequate surface tension to prevent movement of the electrodes, which in practice is unlikely to be a reliable method of adhesion.

The array (and sheet if integrated) may be hermetically sealed before use. To prepare the electrocardiogram sensor ready for a recording, the array (and sheet if integrated) is taken out of its packaging. The module may or may not have been placed into the array but it is easier if it is, so that this does not have to be done when the baby is born. This arrangement is shown in FIG. 4, with the module 301 already in place on the dock 103 of the electrode array 100. This also provides the opportunity to check that all connections are made correctly. The processing and display unit 300 can be turned on to carry out such a check.

The electrocardiogram sensor, comprising the array 100 and sheet 200, is placed on its back, i.e. with the electrical contact surfaces of the electrodes 101*a-d* facing upwards. If the sheet is to be used and packaged separately, the sheet 200 is laid on top of the array 100 so that the holes 201*a-d* on the sheet 200 line up with the electrodes 101*a-d* on the array 100. The sheet 200 can be slightly stretched to force the electrodes 101*a-d* through the holes 201*a-d* in the sheet 200. This will keep the electrodes 101*a-d* in place.

Conductive or wet gel is then applied to the electrodes 101*a-d* and a small amount can be smeared across the sheet 200 (away from the electrodes to prevent short circuits). The sheet/array assembly is left upside down in a convenient location and it is now ready to be applied to the baby's skin when the baby is born. It may for example be left on the resuscitation table upside down if the baby is to be placed on top of the electrode array such that the electrode array contacts the back of the baby.

When the baby is born, the baby is normally brought to the resuscitation table and dried using a towel. Although in premature babies (but not to the exclusion of term babies), it may be that only the head is dried and the body is left wet. This gives the opportunity to use the wet skin as additional surface tension for the array/sheet.

Immediately after this, either the baby is placed on top of the array and sheet face up, or alternatively the whole array with electrodes and sheet is lifted and placed onto the baby. The substrate, gel and sheet, together with the fact that the baby's skin can be wet, helps keep the array stuck to the baby's skin, so that no adhesive is required. The baby can then be placed into another plastic bag if required to prevent hypothermia.

Figure 5:
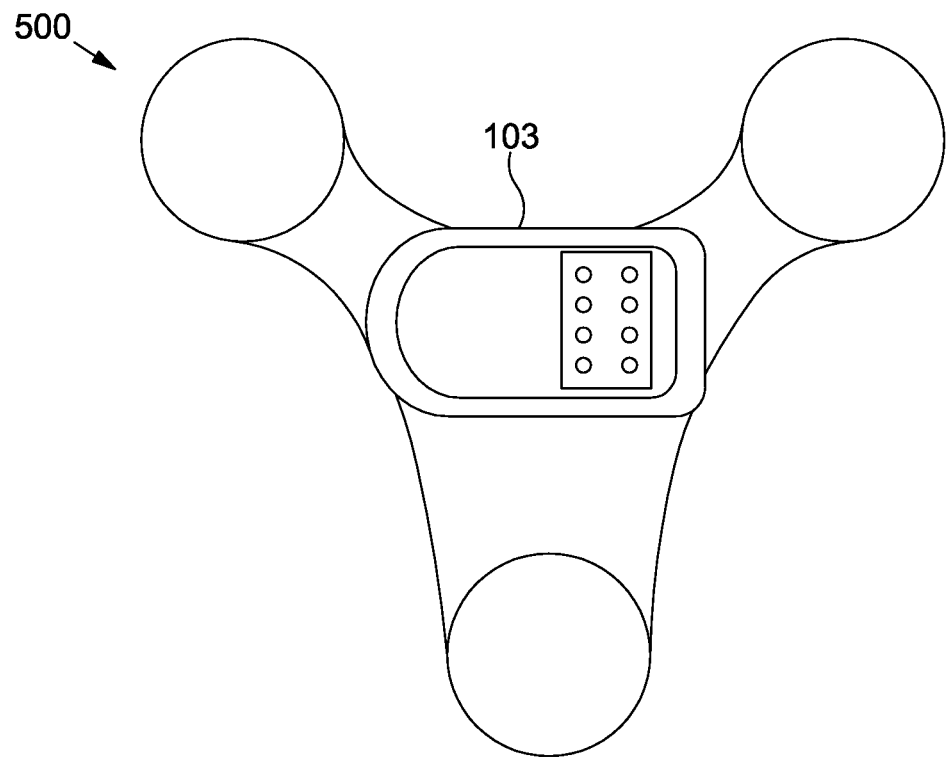
FIG. 5 is a schematic plan view of an alternative example electrode array having a three electrode arrangement and a central dock connector.
Figure 6:
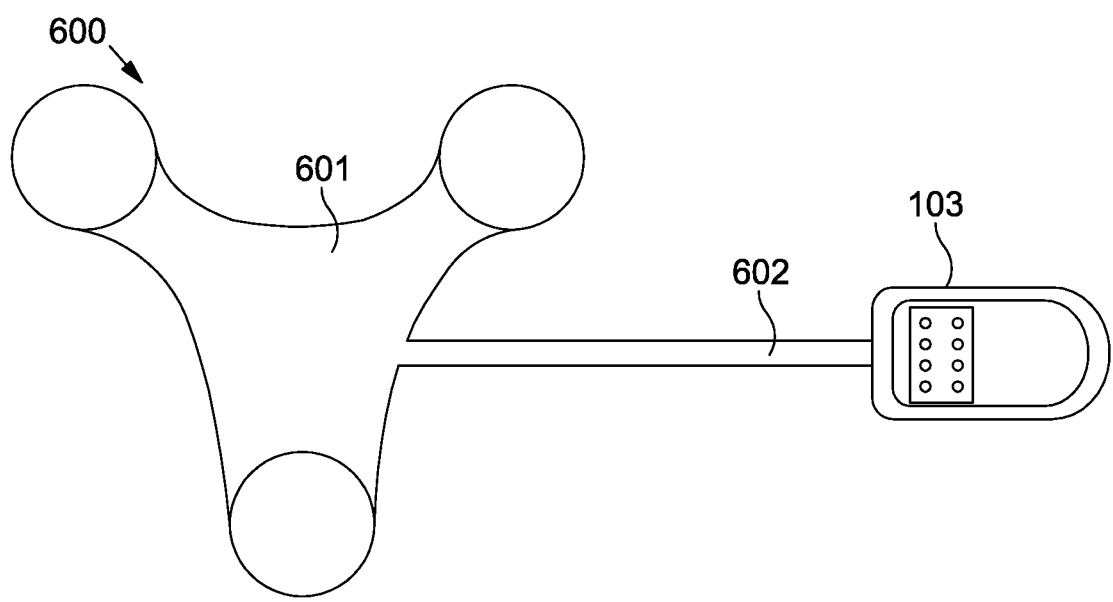
FIG. 6 is a schematic plan view of a further alternative example electrode array, with a dock connector offset from the electrode array.
Figure 7:
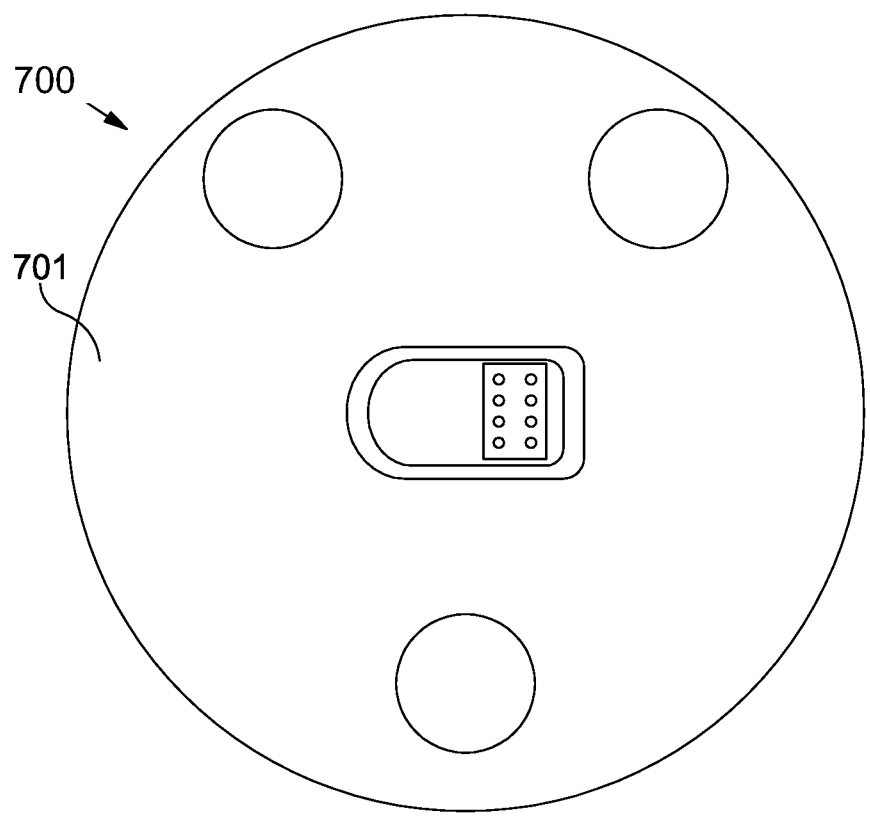
FIG. 7 is a schematic plan view of a further alternative example electrode array with a circular shaped substrate.

FIGS. 5, 6, 7 and 8 illustrate alternative examples of electrode arrays to that shown in FIGS. 1 and 4. A triangular array 500, 600 is illustrated in FIGS. 5 and 6, with the dock 103 positioned within the array in FIG. 5 and in FIG. 6 at the distal end of a connector 602 extending from the substrate 601. An alternative to this is shown in the array 800 illustrated in FIG. 8, where a cable 802 is used in place of a wireless module attached to a dock. FIG. 7 shows a triangular array 700 provided on a circular substrate 701. Other arrangements are also possible.

Figure 9:
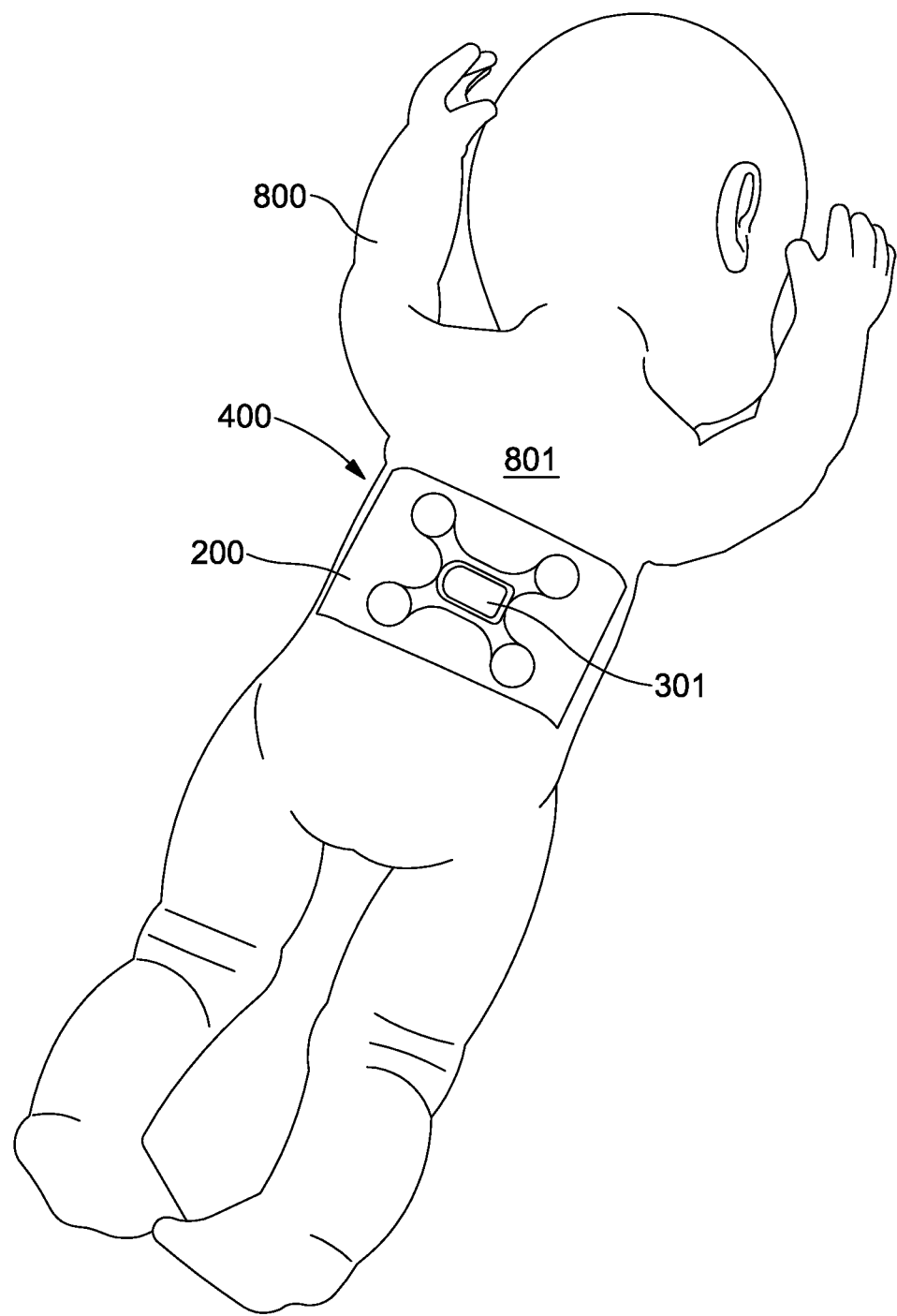
FIG. 9 is a representation of an example electrocardiogram sensor in place on the back of a newborn baby.

FIG. 9 is an illustration of how an electrocardiogram sensor 400 of the type shown in FIG. 4 may be attached to a newborn baby. The sensor 400, with module 301 in place, is positioned on the back 801 of the baby 800. The flexible sheet 200 is extended across the baby's back 801 to provide additional surface tension. In other examples the sheet 200 may be extended further around the baby for additional security. In other examples, the module 301 may be attached to a dock of the form shown in FIG. 6, i.e. at the distal end of a connector extending from the substrate. When attaching the sensor 400 to the back of a baby, this arrangement may be preferred since the module will not be covered when the baby is placed in its back, which may affect wireless transmission and cause discomfort for the baby. This problem may, however, be ameliorated to some extent by the module having a low profile.

Figure 10:
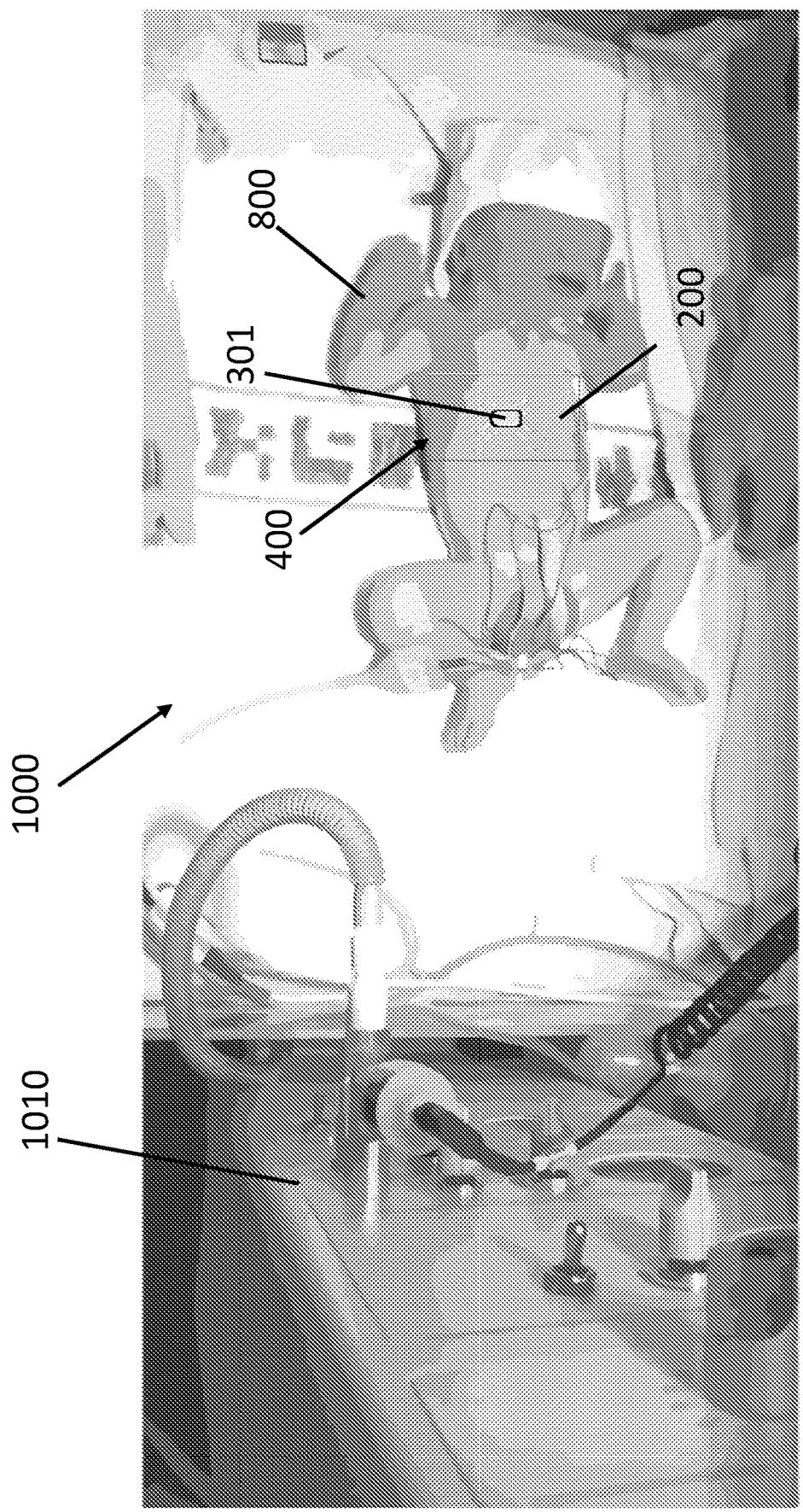
FIG. 10 is an illustration of an embodiment in use on a resuscitation table 1000.

FIG. 10 is an illustration of an electrocardiogram sensor 400 of the type shown in FIG. 4 as may be used in combination with a resuscitation table 1000. The sensor 400, with module 301 in place, is positioned on the chest of the baby 800. The flexible sheet 200 is extended across the baby's chest. A recording unit 1010, comprising the unit 300 of FIG. 3, is placed at the end of the bed.

The unit 300 may comprise at least one camera and/or one microphone. The at least one camera may be a wide angle camera, and may form part of the unit 300 or be removeable. The at least one camera and microphone can be used to capture audio and video of the birth, which is useful for both training purposes and to produce incident reports if necessary. Alternatively, these components may form part of recording unit 1010. The at least one camera and/or microphone may be positioned to monitor the display, the newborn, the ancillary equipment or any other feature of the surrounding environment, or any combination of these.

The at least one camera may be a sensitive wide wavelength camera. This camera can be used to assess the Apgar score of a newborn baby (a measure of health, with criteria of Appearance, Pulse, Grimace, Activity, Respiration). The camera can also allow for non-contact photoplethysmogram analysis and blood oxygen saturation level to be measured. These measurements can be taken to complement the ECG heart rate measurement provided by the electrocardiogram sensor 400.

In summary, a solution is proposed herein to overcomes the problems associated with conventional ECG electrodes which require strong adhesive forces and are difficult to apply to newborns through the use of surface tension on an ECG array which can be rapidly and reliably applied to the newborn baby at birth.

Other embodiments are intentionally within the scope of the invention as defined by the appended claims.

The invention claimed is:

1. An electrocardiogram sensor comprising:
   an electrode array comprising a substrate interconnecting three or more spaced apart electrodes, wherein the electrode array extends to a first areal extent and thereby defines a first surface area encompassing the first areal extent; and
   a flexible sheet that secures the electrodes to the body of a subject by surface tension or dispersive adhesion, wherein the flexible sheet extends beyond the first areal extent to a second areal extent and thereby defines a second surface area encompassing the second areal extent, and wherein the second surface area is greater than twice the first surface area.

2. The electrocardiogram sensor of claim 1 wherein the flexible sheet comprises holes at positions corresponding to the electrodes, each hole being smaller than a corresponding electrode.

3. The electrocardiogram sensor of claim 1 wherein the flexible sheet and the electrodes are non-adhesive.

4. The electrocardiogram sensor of claim 1 wherein the substrate comprises a sheet of a first polymeric material and the flexible sheet comprises a sheet of a second polymeric material, the second polymeric material having a lower stiffness than the first polymeric material.

5. The electrocardiogram sensor of claim 4 wherein the first polymeric material has a tensile stiffness of greater than 2 GPa and the second polymeric material has a tensile stiffness of less than 1 GPa.

6. The electrocardiogram sensor of claim 4 wherein the first polymeric material is polyethylene terephthalate or a polyamide, and/or the second polymeric material is polyethylene or polyvinyl chloride.

7. The electrocardiogram sensor of claim 1 wherein the flexible sheet has a thickness of less than 50 micrometres, less than 25 micrometres or less than 12.5 micrometres.

8. The electrocardiogram sensor of claim 1 wherein the substrate has a thickness of less than 150 micrometres, less than 100 micrometres or less than 50 micrometres.

9. The electrocardiogram sensor of claim 1 wherein the flexible sheet and the substrate are integrated.

10. The electrocardiogram sensor of claim 1 comprising a dock having electrical contacts for contacting with a corresponding module, the electrical contacts connected to the electrodes of the sensor.

11. The electrocardiogram sensor of claim 10 wherein the dock is provided at a distal end of a connector extending from the substrate, or at a central region of the substrate between the electrodes.

12. The electrocardiogram sensor of claim 1 comprising a cable connected to the electrodes via connections on the substrate.

13. An electrocardiogram sensor system comprising:
    the electrocardiogram sensor according to claim 10;
    a module connectable to the dock on the substrate; and
    a processing and display unit wirelessly connectable to the module,
    wherein the module is configured to wirelessly transmit data obtained from the electrodes of the electrocardiogram sensor for display on the processing and display unit.

14. The electrocardiogram sensor system of claim 13, wherein the processing and display unit comprises at least one camera and/or at least one microphone for monitoring the subject.

15. A method of applying an electrocardiogram sensor comprising an electrode array having a substrate interconnecting three or more spaced apart electrodes, wherein the electrode array extends to a first areal extent and thereby defines a first surface area encompassing the first areal extent, and a flexible sheet configured to secure the electrodes to the body of a subject by surface tension or dispersive adhesion, the method comprising:
- applying an electrically conductive gel to each of the electrodes; and
- applying the flexible sheet and the electrodes to the subject,
- wherein the flexible sheet extends beyond the first areal extent to a second areal extent and thereby defines a second surface area encompassing the second areal extent, and wherein the second surface area is greater than twice the first surface area .

16. The method of claim 15 comprising arranging the flexible sheet such that each of the electrodes is aligned with a corresponding hole in the flexible sheet.

17. The method of claim 15 comprising applying a gel, optionally an electrically conductive gel, to a side of the flexible sheet prior to applying the flexible sheet to the subject.

18. The method of claim 13 wherein the subject is a newborn child.

19. The method of claim 18 wherein the electrodes and flexible sheet are applied to the back of the newborn child.

\* \* \* \* \*